United States Patent [19]

Medvinsky

[11] Patent Number: 5,218,303

[45] Date of Patent: Jun. 8, 1993

[54] BROAD SPAN DYNAMIC PRECIOUS METAL ASSAY METHOD BY DRIVING ELECTRICAL PULSES THROUGH AN ELECTROLYTE WET JUNCTION

[76] Inventor: Boris Medvinsky, 355 Oak Branch Dr., Encinitas, Calif. 92024

[21] Appl. No.: 925,747

[22] Filed: Aug. 7, 1992

Related U.S. Application Data

[63] Continuation-in-part of Ser. No. 775,098, Oct. 11, 1991, abandoned.

[51] Int. Cl.$^5$ .................. G01N 27/26; G01N 27/42
[52] U.S. Cl. .................. 324/425; 204/153.1; 324/71.1; 324/444
[58] Field of Search .................. 324/71.1, 425, 439, 324/444; 204/153.1, 400, 406

[56] References Cited

U.S. PATENT DOCUMENTS

| | | | |
|---|---|---|---|
| 4,179,349 | 12/1979 | Park | 204/400 X |
| 4,190,501 | 2/1980 | Riggs, Jr. | 204/400 X |
| 4,376,027 | 3/1983 | Smith et al. | 204/406 |
| 4,799,999 | 1/1989 | Medvinsky et al. | 204/153.1 |

Primary Examiner—Gerard R. Strecker
Assistant Examiner—Diep Do
Attorney, Agent, or Firm—John J. Murphey

[57] ABSTRACT

A dynamic precious metal assay which includes the steps of introducing a controlled amount of liquid electrolyte onto a sample of precious metal alloys, placing an inert electrode in contact with the sample in the presence of the electrolyte to create a wet junction, driving a first pulse of electric current through the electrolyte in the wet junction to cause an oxidation/reduction reaction of the alloying materials present in the alloyed sample to form an electrolytic-based paste, terminating the electric current and allowing the current in the paste to decay to an asymptotic level, driving a second pulse of electric current through the electrolytic paste in the junction at an amplitude above the asymptotic level, driving a third pulse of electric current, at a higher amplitude than the second pulse, through the electrolytic paste in the junction, instantaneously measuring the electrolytic conductance of the electrolytic paste, comparing the conductance with an empirical table of electrolytic paste conductance standards, interpolating the conductance by differentiation against the empirical table of standards, and announcing the interpolation.

20 Claims, 3 Drawing Sheets

| METAL | PASTE CONDUCTANCE (reported in Milliamps) |
|---|---|
| Platinum | 23MA< |
| 24K (pure) | 23MA> <27MA |
| 23K | 27MA> <28MA |
| 22K | 28MA> <34MA |
| 21K | 34MA> <36MA |
| 20K | 36MA> <38MA |
| 18K | 38MA> <40MA |
| 16K | 40MA> <41MA |
| 14K | 41MA> <43MA |

| METAL | PASTE CONDUCTANCE (reported in Milliamps) |
|---|---|
| NO GOLD | 51MA> |
| 5K | 50MA> <51MA |
| 6K | 49MA> <50MA |
| 8K | 47MA> <49MA |
| 10K | 45MA> <47MA |
| 12K | 43MA> <45MA |
| 14K | 41MA> <43MA |
| 16K | 40MA> <41MA |
| 18K | 38MA> <40MA |
| 20K | 36MA> <38MA |
| 21K | 34MA> <36MA |
| 22K | 28MA> <34MA |
| 23K | 27MA> <28MA |
| 24K (pure) | 23MA> <27MA |

BROAD SPAN DYNAMIC PRECIOUS METAL ASSAY METHOD BY DRIVING ELECTRICAL PULSES THROUGH AN ELECTROLYTE WET JUNCTION

RELATION TO OTHER PATENT APPLICATIONS

This application is a continuation-in-part of my previously filed patent application titled BROAD SPAN DYNAMIC PRECIOUS METAL ASSAY METHOD AND APPARATUS THEREFOR, filed Oct. 11, 1991, given Ser. No. 07/775,098, and now abandoned.

BACKGROUND OF THE INVENTION

1. Field of the Invention

This invention relates to a method for testing metals. More particularly, the invention relates to a method of determining the amount of gold or other precious metal in an alloy and reporting it. In gold samples, the gold content is reported as "karatage".

2. Description of the Prior Art

Metal alloys are homogeneous in content and it is generally considered virtually impossible to determine the content of any specific metal in an alloy by visual observation. Historically, the content of a specific metal in an alloy of metals is determined by qualitative and quantitative chemical analysis occurring in a laboratory which requires grinding the metal to obtain a sample, solubilizing the sample with acid and titrating the solution against a known standard; all resulting in partial loss of the metal.

Beginning in late 1979, electricity was combined with chemical electrolytes in a small device to determine the presence or absence of certain metals in an alloy composition. U.S. Pat. No. 4,179,349 concerns the use of a probe containing an electrolyte that is placed in electrical contact with a test piece of metal alloy to determine through voltage-current profiles the presence or absence of chromium in stainless steels that had been subjected to extended heat such as to become "sensitized". This device measured only the presence or absence of chromium and not any quantitative amounts thereof.

Later, U.S. Pat. No. 4,240,892 discloses a similar device using chemical electrolytes placed in physical and electrical contact with a metal alloy test specimen to determine the relative anodic properties of metals that had been subjected to shaping or bending to determine its propensity for corrosion. Again, no quantitative analysis is possible by this invention. Another U.S. Pat. No. 4,376,027 discloses a compact, self-contained portable electrolytic testing device for placement against a metal alloy to provide an electronic current through a deposit of color responsive electrolyte to determine the presence of a specific metal. Again, no quantitative analysis is possible by this device.

The inventor's previously issued U.S. Pat. No. 4,799,999, discloses a method for determining the assay of gold alloy between about six to about 14-karat gold utilizing an electrolyte deposited on a sample of precious metal such as to create a wet junction and driving an electric current through the electrolyte to anodize the junction and thereafter terminating the electric current and monitoring the decay in the potential of the sample at the wet junction and comparing the one-time measured potential during the decay period with an empirical table of standards and interpolating and reporting the result. This invention, while capable of reporting accurate results, is limited to the lower end of the scale of gold-containing alloys, namely those in the area of about six to about 14-karat gold. Higher karatage gold alloy does not respond significantly to the method disclosed in said patent, i.e., from 14 to 24-karat gold gives the same result by this method.

SUMMARY OF THE INVENTION

The instant invention is based in part upon the discovery that while measurement of potential decay at the test site is functional to determine the purity of the sample in the lower ranges of gold karatage, a measure of the electrolytic conductance of the junction during the imposition of a low-level current across the junction provides unprecedented accuracy in the determination of noble metals in alloys of higher noble metal content, such as those between 14 and 24 karat gold. Further, it has been determined that the inventory of acid electrolyte, usually retained in a pen-shaped tool next to the electrode, undergoes irreversible changes during testing such that the accuracy of later tests is reduced. Still further, it has been determined that the amount of fresh electrolyte deposited on the test sample is critical to the accuracy of the reported results and, where the volume of the electrolyte is controlled to provide a constant volume for each test, the results between tests are made far more reliable.

One embodiment of the invention generally comprises a process by which a controlled amount of electrolyte is deposited on the test sample and a half-cell or electrode of platinum or gold joined therewith. A first current pulse is passed between the sample and the electrode, across an accurately established separation distance containing electrolyte, for a set period of time, in order to create an oxidation/reduction reaction of the alloying metals at the point of contact to produce a paste of ions in the electrolyte. The current is then terminated and the potential allowed to decay to an asymptotic level.

Thereafter, a second current having an amplitude slightly greater than the asymptotic value of decay is applied across the junction and, during the second current, a burst of current of far greater amplitude is driven across the paste and the electrolytic conductance of the paste is instantaneously measured and passed through a differential amplifier, into a microcomputer where the analog value of the conductance is converted to a digital response. The digital response is thereafter compared to a set of values previously stored in a memory in the microcomputer representing the conductance of pastes of various samples of known karatage, and the reported value interpolated against the known values and the results reported on a liquid crystal display board for optical readout by the tester.

In another embodiment of the invention, the first current pulse is passed between the sample and the electrode, and then terminated and the potential allowed to decay to an asymptotic level, as previously described. Just prior to the current pulse being terminated, the voltage drop across the junction is measured and processed through an analog-to-digital converter to a digital value, as "$U_2$" and stored in a memory unit. I call this method the "voltage versus current method". For lower karatage of gold, i.e. where more copper and silver are alloyed with the pure gold, the current across the junction will be higher than for higher karatages of gold and the lower voltage termed "$U_2$" (as will be later more full explained) will drop across the wet junction. This method points up a $U_2$ voltage range from about 0.90 volts to about 2.00 volts for karatages of from about 5 to about 24 (pure gold).

Thereafter, a second current having an amplitude slightly greater than the asymptotic value of decay is applied across the junction and, during the second current, a burst of current of far greater amplitude is driven across the paste and the electrolytic conductance of the paste is instantaneously measured and passed through a differential amplifier, converted to a voltage ($U_1$), and then passed into a microcomputer where the analog value of the conductance is converted to a digital response and stored in a memory.

Using the formula $$U = \frac{U_1 - U_2}{U_1 + U_2}$$

provides the determination of U. This calculated value is then compared to a set of values of U, previously determined from tests of samples of known karatages of gold, inputted into the memory and the value interpolated thereagainst. The result is then presented on a liquid crystal display for optical readout by the user. Using the second method to calculate the value of U provides a more accurate result, increases the range of karatage that may be determined, and provides more temperature stability to the method.

In contrast to prior art devices where the electrode is housed in a tool or device that also contains an inventory of electrolyte, this invention utilizes an electrode that is retained in a hollow tool, in a geometry having a set physical size so that the electrolyte deposited therein on the platinum electrode prior to the test is of a known volume. The combination of consistency in volume of electrolyte and the special application of electric currents to the test sample results in an extremely high degree of accuracy for determination of amounts of noble metal throughout the entire range of alloys and is a significant step forward in the state-of-the-art that, until now, could only report measurements in the lower end of noble metal alloys. Further, in contrast to the prior art technology, the electrode is adapted to be fully exposed both before and after the test so that it may be cleaned (along with the test sample) with a small quantity of fresh electrolyte to remove all traces of old electrolyte or paste.

Except for the tool holding the platinum electrode and the reservoir carrying the electrolyte, the entire test apparatus may be constructed using micro chips and other small circuit components so that the device may be conveniently enclosed in a container that is comfortably held in one hand. A dry test tool is also easily handled and is far safer than prior art devices that contained a quantity of acidic electrolyte. Electrolyte attacks virtually every metal, human skin, many plastics and is thus hard to handle. By containing the electrolyte in a separate safe container and rendering the test tool empty of electrolyte, the resulting test equipment is far more amenable to safe storage, has a greater storage life, and is far safer to use than heretofore available in the prior art. The prior art test devices have reservoirs of electrolyte adjacent the test probes. With such an inventory in such close proximity to the test probes, it is difficult if not impossible to totally clean the test probes of electrolyte used in the previous test. This residue brings a certain amount of inaccuracy into subsequent tests. The new test probe of this invention has no such internal reservoir and is thus capable of a far greater degree of cleaning to give far more accurate results.

Accordingly, the main object of this invention is a broad spectrum dynamic precious metal assay method that produces far more accurate noble metal readings or gold karatage readings over the entire spectrum of noble metal alloys than heretofore obtainable in the prior art. Other objects include a device that incorporates small, solid state microcomputer components and three current generators that are easily and conveniently housed in a rugged and safe structure the size of which is easily carried in one's hand; a device that uses a half-cell test tool totally free of harsh and acidic electrolytes to achieve a longer shelf life and pose a lesser risk to other components utilized in the system; a device that quickly, conveniently and accurately measures the purity of noble metal alloys, especially gold purity of gold-containing alloys, and is amenable to providing a digital, easily-read display of the exact karatage or purity of the noble metal in the test sample; a method of utilizing the testing device that is easily powered by a small 9-volt battery or that may be connected to ordinary house current to provide accurate amounts of current to facilitate the testing procedures; a device that measures the electrolytic conductance of the paste created by the alloy ions that are formed when the electrolyte is subject to electrical current, that does not rely upon decay potentials or other decayrelated properties but measures the exact electrolytic conductance of the paste and converts the value to a voltage $U_2$; measures the voltage $U_1$ of the voltage versus current characteristics of the paste and calculates the value of U using the formula $$U = \frac{U_1 - U_2}{U_1 + U_2}$$

to provide a more accurate analysis of the noble metal in the sample.

These and other objects of the invention will become clear to those who read the following description of the preferred embodiment taken together with the drawings. The scope of protection sought by the inventor may be gleaned from a fair reading of the claims that conclude this specification.

DESCRIPTION OF THE PREFERRED EMBODIMENTS

Figure 1:
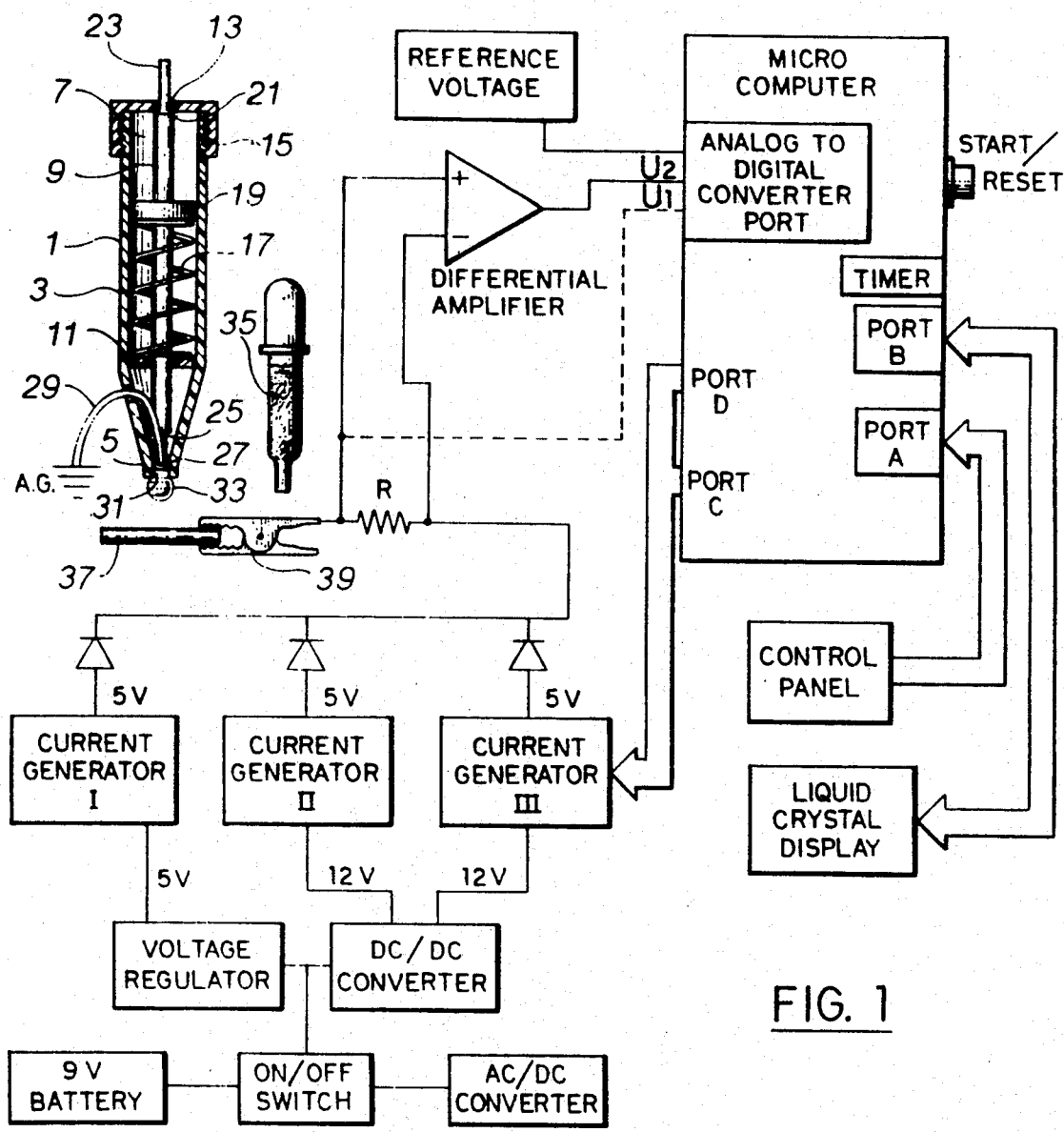
FIG. 1 is a side elevational view of the preferred embodiment of the test probe and its associated hardware and electronic components.

The invention uses an electric cell comprising a reference cathode of platinum and an anode which is the specimen or sample under test. The electrolyte is conventionally a one and one-half percent aqueous hydrochloric acid solution to which is added a sufficient amount of gelling material to create a soft gel. Gelling has been found to hold the electrolyte near the contact point between the electrode and the test sample and confine the current applied there between to provide more accuracy in the reported results.

A hand-held tool is used in practicing this invention. Said tool is generally identified in FIG. 1 at 1 and comprises a hollow tube 3, preferably straight and short enough to be held in one's hand, having a lower pointed end 5 and an upper open end 7. A straight, thin shaft 9 is positioned for reciprocal movement inside tube 3 and held in axial alignment therein by at least one centering saddle 11 and a central aperture 13 formed in a cap 15 that is threaded over upper tube end 7. A coiled spring 17 is wrapped about shaft 9 and positioned interior of tube 3, restrained between saddle 11 and an upset 19 formed on shaft 9, to bias shaft 9 upward and forcing a shoulder 21 formed in shaft 9 near the upper end 23, to butt against cap 15 so that upper end 23 of shaft 9 is established a set distance above cap 15. Spring 17 causes the lower end 25 of shaft 9 to be biased upward and inward from pointed end 5 a set distance, i.e., until shoulder 21 abuts the underside of cap 15. Tube 3, shaft 9, and cap 15 are all constructed preferably from electrically non-conductive material such as polyvinylchloride plastic and the like.

The length of shaft 9, from lower terminal end 25 to upset 19 is carefully set. A small, inert platinum electrode 27 is affixed to lower shaft end 25 and connected to a wire 29 that exits tube 3 and is attached to an analog ground (A.G.). Electrode 27 is sized to pass through an aperture 31 formed in lower tube pointed end 5 when one presses downward on shaft terminal end 23. It is preferred that electrode 27 have a flat face formed on the surface thereof to facilitate the flow of electrons between electrode 27 and the surface of the test sample. Also, by pressing shaft terminal end 23 downward, electrode 27 can be fully exposed outside and beyond tube 3. Shoulder 21 is set to allow electrode 27 to dwell just inside the opening of lower tool pointed end 5 such as about 40/1000 of an inch. During the test, electrode 27 is maintained at this distance from the test sample so that the results are consistent. Upper end 23 of shaft 9 is used to expose electrode 27 out of lower tool pointed end 5 to allow it to be cleaned of old electrolyte or paste between tests. By releasing upper end 23, electrode 27 is biased upward and withdrawn back into its set position of 40/1000 of an inch in from the end of the tool.

Figure 1A:
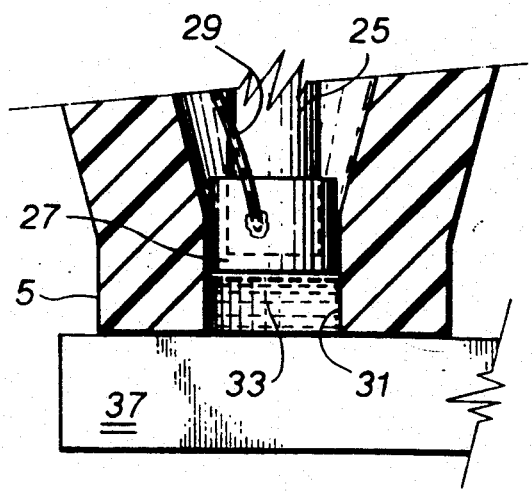
FIG. 1a a close-up view of the wet junction formed between the and the test sample.

As further shown in FIG. 1, a small drop 33 of liquid electrolyte is dispensed from a convenient source, such as from a dropper 35, into lower tool pointed end 5 in aperture 31 on electrode 27 and then the tool is lowered onto the metal sample 37. The electrolyte between electrode 27 and the surface of metal sample 37 forms a wet junction therewith as shown in FIG. 1a.

There are two inventive methods usable in this invention, especially with alloys containing different noble metals. The following explanations are directed to gold alloys. In the first method, and referring to FIG. 1, electrical power, either from a 9-volt battery or from an AC/DC converter, passes through an off/on switch and through a voltage regulator and DC/DC converter to provide accurate voltages to three current generators, I, II and III, respectively, in values such as 5-volts and 12-volts. Each current generator is connected to a separate diode whose outputs are connected in series to one end of current measuring resistor R and simultaneously inputted to the non-inverting side of a differential amplifier. The other side of resistor R is connected to alligator clip 39 and inputted into the inverting side of said differential amplifier. The output of the differential amplifier is connected to the first input of an analog-to-digital converter at the input/output port of the microcomputer. A reference voltage is connected to the A/D converter while a control panel is connected to Port A of the microcomputer.

Figures 2, 3:
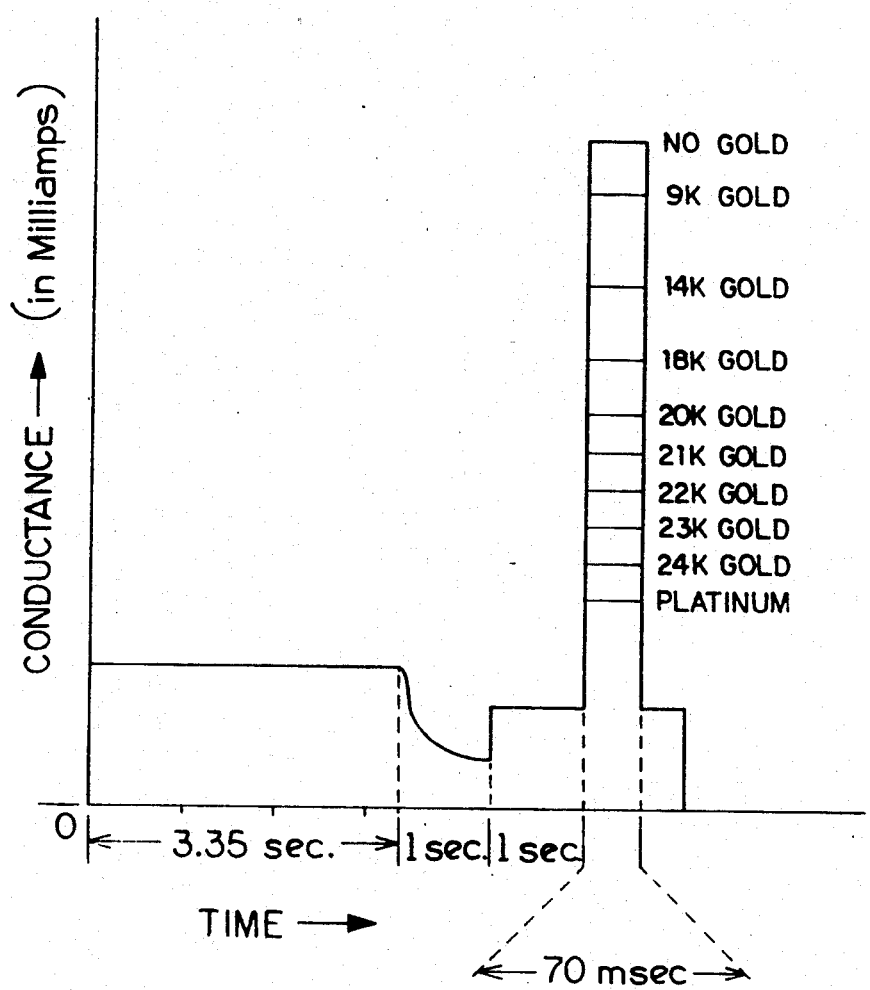
FIG. 2 is a graph of current versus time of the electrochemical cell the first method.
FIG. 3 is a table of electrolytic conductance values of gold alloys found by the first method.

As shown in FIG. 2, and initial pulse of current of about 1 to 4 milliamps is passed from current generator I through its respective diode, resistor R, sample 37, through electrolyte 33, into electrode 27, out wire 29 and into analog ground A.G. The length of time the current is passed may vary but it is preferred to last between about 3-4 seconds and specifically 3.35 seconds. This current causes an oxidation/reduction reaction to occur with the metals, such as copper and silver, that have been alloyed with the pure gold to establish the appropriate karatage to be determined. Gold is non-reactive and thus does not enter into the reaction. The result is an electrolyte paste being formed containing ions of the alloying metal between test sample 37 and platinum electrode 27.

Before this first pulse is terminated, the voltage or potential at the wet junction is measured between anode—sample 37 and cathode—inner electrode 27 and that value is converted to a digital response at the A/D convertor and stored in the memory of the microcomputer and labeled $U_2$.

After this initial current, the microcomputer orders a cessation of the current such that, over the next second or so, no current is supplied thereby allowing the current remaining in the paste to quickly decay to an asymptotic level as shown in FIG. 2. After this asymptotic level is reached, a second pulse of current of about 0.2 milliamps, is passed through the paste from current generator II for a period of time such as for approximately one second. This current aligns the ions in the paste and produces more consistent and accurate results.

Thereafter, a third pulse of current is then passed through the paste from third current generator III in a burst of about 70 milliseconds in duration. The electrolytic conductance of the paste is thereafter instantaneously and carefully measured across resistance R by the differential amplifier connected as shown in FIG. 1. The analog results are preferably fed to the analog-to-digital converter in the microcomputer for comparison with a set of known electrolytic conductance values such as shown in FIG. 3, previously stored in the memory of the microcomputer. The extrapolated value is then transmitted to a liquid crystal display for a direct readout of the gold karatage by the tester.

As shown in FIGS. 2 and 3, the higher amount of gold (greater karatage) in test sample 37 will cause a lower conductance across the paste, between test sample 37 and electrode 27, because of the lesser amount of ions presently due to the lower amount of alloying metals. By sampling the electrolytic conductance of various samples and comparing the measured value with an electronic look-up table, the microprocessor can interpolate the various values to evaluate the percentage of gold in the test specimen and display the evaluation in units of karatage on the liquid crystal display.

In the second method of this invention, the circuitry of FIG. 1 is altered slightly to provide for a separate conductor, shown in dotted line, branching off from resistor R bypassing the differential amplifier and inputting directly to the analog-to-digital convertor port.

Figures 4, 5:
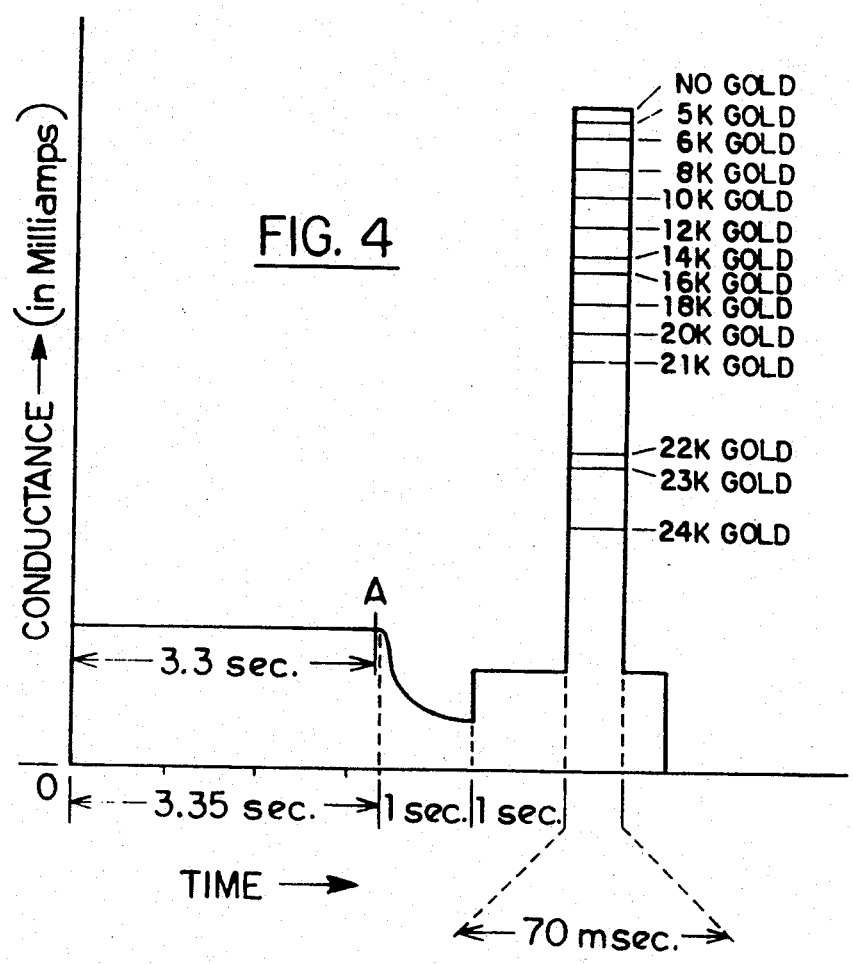
FIG. 4 is a graph of current versus time of the electrochemical chemical cell for the second method; and, FIG. 5 is a table of electrolytic conductance values of gold alloys found by the second method.

In this second method, before the first pulse is terminated, i.e., such as at about 3.30 seconds into the first pulse, the measurement of potential of the wet junction between anode 37 and cathode 27 is taken (shown at point "A" in FIG. 4) and inputted as value $U_1$ to the A/D convertor port where it is converted to a digital response and stored in the memory of the microcomputer. The voltage $U_1$ has a range from about 0.9 volts to about 2.0 volts reflecting a karatage of from about 5 to about 24. After this initial current, the microcomputer orders a cessation of the current such that, over the next second or so, no current is applied thereby allowing the current in the paste to quickly decay to an asymptotic level as shown in FIG. 4. After this interval, a second pulse of a current of about 0.2 milliamps, is passed through the paste from current generator II, through resistor R for a period of about approximately one second. This current, again, aligns the ions in the paste and produces more consistent and accurate results.

A third pulse of current is then passed through the paste from current generator III in a burst of about 70 milliseconds in duration. The electrolytic conductance of the paste in the wet junction between the anode and cathode is thereafter instantaneously and carefully measured across resistor R by the differential amplifier connected as shown in FIG. 1. The output of the differential amplifier in this case gives a result in value of voltage termed $U_2$ that is proportional to the electrolytic conductance of the wet junction between the anode (test material) and the cathode. The analog results of $U_2$ are preferably fed to an analog-to-digital convertor in the microcomputer and converted to a digital response and stored in the memory. Using the formula $$U = \frac{U_1 - U_2}{U_1 + U_2}$$

and calculating the value of U for various samples and then comparing this value with an electronic look-up table, stored in the computer memory, the microcomputer can interpolate the various values to evaluate the percentage of gold in the test specimen and display the evaluation in units of karatage of gold on the liquid crystal display. This latter method provides far more accurate readings than the first method because of the two values of U. These new values are shown in FIG. 5.

There is a start button which resets all of the circuits and initiates the timer of the microcomputer. There is a microcomputer that controls the current pulses. There are sample and hold circuits which work in conjunction with the analog-to-digital converter which build up in the miorocomputer. The whole test procedure takes on the order of five to seven seconds and the results are reported forthwith. Because of the short duration of exposure time of the test sample to the acidic electrolyte, there is virtually no destruction or damage to the test specimen.

Prior to the beginning of the test, platinum electrode 27 is moved totally out of tool 1 so that it may be cleaned with a small quantity of fresh electrolyte to remove traces of paste or electrolyte from past tests. Similarly, the test spot on test sample that is going to be tested is cleaned with some fresh electrolyte.

At the end of the test, the test specimen as well as platinum electrode 27 are cleaned by wiping with a cloth containing a small amount of a fresh electrolyte. By releasing pressure on upper shaft end 23, coil spring 17 urges shaft 9 upward and retracts platinum electrode 27 inside lower pointed tool end 5 for protection from the elements and from physical damage, ready for further testing. A simple temporary clip, such as alligator clip 39 may be used to connect current generators I, II and III through resistor R to the test specimen 37.

Some electrical wiring in these drawings have not been shown for clarity; such wiring is already known in the prior art. Where wires cross or intersect and there is a dot shown therewith, it is to be considered that there is an interconnection between the wires. Where wires cross and no dot is shown, it is to be considered that there is no interconnection therebetween. While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the same way to achieve the same results are within the scope of this invention.

What is claimed is:

1. A dynamic precious metal assay method which comprises the steps of:
   (a) introducing a controlled amount of liquid electrolyte onto a sample of precious metal alloys;
   (b) placing an inert electrode in contact with said sample in the presence of said electrolyte to create a wet junction;
   (c) driving a first pulse of electric current through said electrolyte in said wet junction to cause an oxidation/reduction reaction of the alloying materials present in the alloyed sample to form an electrolytic-based paste;
   (d) terminating said electric current and allowing said current in said paste to decay to an asymptotic level;
   (e) driving a second pulse of electric current through said electrolytic paste in said junction at an amplitude above said asymptotic level;
   (f) driving a third pulse of electric current, at a higher amplitude than said second pulse, through said electrolytic paste in said junction;
   (g) instantaneously measuring the electrolytic conductance of said electrolytic paste;
   (h) comparing said conductance with an empirical table of electrolytic paste conductance standards;
   i) interpolating said conductance by differentiation against said empirical table of standards; and,
   (j) announcing said interpolation.

2. The dynamic precious metal assay method of claim 1 wherein the step of introducing an electrolyte includes the step of introducing a gelled electrolyte containing about 1 and 1½% aqueous hydrochloric acid onto said sample of precious metal alloy.

3. The dynamic precious metal assay method of claim 1 wherein said step of placing an inert electrode includes the step of placing a platinum electrode in contact with said sample.

4. The dynamic precious metal assay method of claim 1 wherein said step of driving a first pulse of electric current through said electrolyte includes the step of driving a pulse of electric current on the order of about 3 to 4 milliamps of direct current of a pulse duration of between about 3 to 4 seconds.

5. The dynamic precious metal assay method of claim 4 wherein the pulse duration is about 3.35 seconds.

6. The dynamic precious metal assay method of claim 1 wherein the step of allowing the current to decay to an asymptotic level includes the step of allowing the decay to last on the order of about one second.

7. The dynamic precious metal assay method of claim 1 wherein the step of driving a second pulse of electric current through said electrolytic paste in said junction includes the step of driving a pulse of electric current on the order of about 0.2 milliamps of direct current through said electrolytic paste.

8. The dynamic precious metal assay method of claim 1 wherein the step of driving a third pulse of electric current through said electrolytic paste in said junction includes the step of driving a pulse of electric current for the duration of about 70 milliseconds.

9. The dynamic precious metal assay method of claim 1 including the further step of initiating an analog-to-digital conversion and outputting a signal from said conversion and storing said signal in a memory.

10. The dynamic precious metal assay method of claim 1 further including the step of displaying said interpolation on a digital readout.

11. A dynamic precious metal assay method which comprises of the steps of:
(a) introducing a controlled amount of liquid electrolyte onto a sample of precious metal alloys;
(b) placing an inert electrode in contact with said sample in the presence of said electrolyte to create a wet junction;
(c) driving a first pulse of electric current through said electrolyte in said wet junction a spaced distance from said sample to cause an oxidation/reduction reaction of the alloyed sample to form an electrolytic-based paste;
(d) measuring the voltage across said wet junction before the first pulse is terminated and converting the value to a digital response through an analog-to-digital converter and storing said value in a memory as "$U_1$";
(e) terminating said electric current and allowing said current in said electrolytic paste to decay to an asymptotic level;
(f) driving a second pulse of electric current through said electrolytic paste in said junction at an amplitude of about 0.2 milliamps of current above said asymptotic level;
(g) driving a third pulse of electric current through said electrolytic paste in said junction, at a higher amplitude than said second pulse;
(h) instantaneously measuring the electrolytic conductance of said electrolytic paste at said wet junction, converting said value of conductance to a value of voltage and labeled "$U_2$", and converting the analog signal $U_2$ to a digital value by an analog-to-digital converter and storing said value in said memory;
(i) calculating the value of U using the formula $$U = \frac{U_1 - U_2}{U_1 + U_2};$$

(j) comparing said value of U with an empirical table of electrolytic paste-based conductance standards;
(k) interpolating said value of U by differentiation against said standards; and
(l) reporting said interpolation.

12. The dynamic precious metal assay method of claim 11 wherein the step of introducing an electrolyte includes the step of introducing a gelled electrolyte containing about 1 and 1½% aqueous hydrochloric acid onto said sample of precious metal alloy.

13. The dynamic precious metal assay method of claim 11 wherein said step of placing an inert electrode includes the step of placing a platinum electrode in contact with said sample.

14. The dynamic precious metal assay method of claim 11 wherein said step of driving a first pulse of electric current through said electrolyte includes the step of driving a pulse of electric current on the order of about 1 to 2 milliamps of direct current of a pulse duration of between about 3 to 4 seconds.

15. The dynamic precious metal assay method of claim 14 wherein the pulse duration is about 3.35 seconds.

16. The dynamic precious metal assay method of claim 11 wherein the step of allowing the current to decay to an asymptotic level includes the step of allowing the decay to last on the order of about one second.

17. The dynamic precious metal assay method of claim 11 wherein the step of driving a second pulse of electric current through said electrolytic paste in said junction includes the step of driving a pulse of electric current on the order of about 0.2 milliamps of direct current through said electrolytic paste.

18. The dynamic precious metal assay method of claim 11 wherein the step of driving a third pulse of electric current through said electrolytic paste in said junction includes the step of driving a pulse of electric current for the duration of about 70 milliseconds.

19. The dynamic precious metal assay method of claim 11 including the further step of initiating an analog-to-digital conversion and outputting a signal from said conversion and storing said signal in a memory.

20. The dynamic precious metal assay method of claim 11 further including the step of displaying said interpolation on a digital readout.

* * * * *